United States Patent
Zhang et al.

(10) Patent No.: US 6,645,367 B1
(45) Date of Patent: Nov. 11, 2003

(54) METHOD FOR DETERMINING A NITROGEN OXIDE CONCENTRATION

(75) Inventors: Hong Zhang, Tegernheim (DE); Jürgen Rössler, Münnerstadt (DE)

(73) Assignee: Siemens Aktiengesellschaft, Munich (DE)

(*) Notice: Subject to any disclaimer, the term of this patent is extended or adjusted under 35 U.S.C. 154(b) by 0 days.

(21) Appl. No.: 09/699,599

(22) Filed: Oct. 30, 2000

Related U.S. Application Data

(63) Continuation of application No. PCT/DE99/01091, filed on Apr. 9, 1999.

(30) Foreign Application Priority Data

Apr. 30, 1998 (DE) .......................................... 198 19 462

(51) Int. Cl.[7] ............................................. G01N 27/407
(52) U.S. Cl. ........................ 205/781; 204/425; 204/426; 204/427
(58) Field of Search ............................... 204/421–429; 205/781, 783–785

(56) References Cited

U.S. PATENT DOCUMENTS

| | | |
|---|---|---|
| 4,981,125 A | 1/1991 | Kato et al. |
| 5,033,438 A | 7/1991 | Feldinger et al. |
| 5,034,112 A | 7/1991 | Murase et al. |
| 5,928,494 A * | 7/1999 | Kato et al. |
| 6,059,947 A * | 5/2000 | Kato et al. |
| 6,171,470 B1 * | 1/2001 | Patrick et al. |
| 6,375,828 B2 * | 4/2002 | Ando et al. |

FOREIGN PATENT DOCUMENTS

| | | |
|---|---|---|
| DE | 35 39 395 A1 | 5/1987 |
| DE | 43 21 156 A1 | 5/1994 |
| DE | 44 33 044 A1 | 3/1996 |
| EP | 0 810 430 A2 | 12/1997 |
| EP | 0816836 A2 * | 1/1998 |

OTHER PUBLICATIONS

"Performance of Thick Film NOx Sensor on Diesel and Gasoline Engines" (Kato et al.), Society of Automotive Engineers, 1997, pp. 199–206.

* cited by examiner

*Primary Examiner*—T. Tung
(74) *Attorney, Agent, or Firm*—Laurence A. Greenberg; Werner H. Stemer; Ralph E. Locher

(57) ABSTRACT

The $NO_x$ concentration in a gas is determined with a thick-film measuring sensor which has two measuring cells. The raw measured value of the measuring sensor is corrected by a multiplicative correction value and an additive correction value, which are both taken from a characteristic map. The characteristic map depends on the oxygen-ion pumping current in the second measuring cell, the measured gas temperature, and the measuring sensor temperature.

7 Claims, 2 Drawing Sheets ved under specific conditions, in particular at various temperatures, NO$_x$ concentrations, rates of NO$_x$ change etc., and which depends at least on the second oxygen-ion pumping current, preferably in addition on the temperature of the gas to be measured and/or the temperature of the measuring sensor, since the residual oxygen content causing

METHOD FOR DETERMINING A NITROGEN OXIDE CONCENTRATION

CROSS-REFERENCE TO RELATED APPLICATION

This is a continuation of copending international application PCT/DE99/01091, filed Apr. 9, 1999, which designated the United States.

BACKGROUND OF THE INVENTION

Field of the Invention

The invention relates to a method for determining the NO$_x$ concentration in a gas, in particular in the exhaust gas of an internal combustion engine. The concentration is measured with a measuring sensor having a first measuring cell into which part of the gas is introduced and in which a first oxygen concentration is adjusted by means of a first oxygen-ion pumping current, and a second measuring cell, which is connected to the first measuring cell and in which a second oxygen concentration is adjusted by means of a second oxygenion pumping current. The NO$_x$ concentration is measured with a measuring electrode in the second measuring cell.

For measuring the NO$_x$ concentration in a gas, for example in the exhaust gas of an internal combustion engine, it is known to use a thick-film measuring sensor. Such a measuring sensor is described in the publication by N. Kato et al., "Performance of Thick Film NO$_x$ Sensor on Diesel and Gasoline Engines", Society of Automotive Engineers, publication 970858, 1997. This measuring sensor has two measuring cells and consists of a zirconium oxide that conducts oxygen ions. It realizes the following measuring concept: in a first measuring cell, which is fed the gas to be measured via a diffusion barrier, a first oxygen concentration is set by means of a first oxygen-ion pumping current, with no decomposition of NO$_x$ taking place. In a second measuring cell, which is connected to the first measuring cell via a diffusion barrier, the oxygen content is further reduced by means of a second oxygen-ion pumping current and NO$_x$ decomposes at a measuring electrode. The oxygen generated in this way is sensed as a measure of the NO$_x$ concentration. The entire measuring sensor is in this case brought to an elevated temperature, for example 430° C., by means of an electric heater. The measuring error of the measuring sensor described in this publication corresponds to an NO$_x$ concentration of 22 ppm.

The measuring error applies to steady-state operation, i.e. when no great changes in concentration are to be measured. A residual oxygen content in the second measuring cell, which does not originate from a decomposition of NO$_x$, leads to this measuring error, since the oxygen in the second measuring cell is taken as a measure of the NO$_x$ concentration.

In addition, the measuring error of the NO$_x$ measuring sensor described is strongly temperature-dependent. The cause of this is that the first measuring cell is connected to the gas to be measured via one diffusion barrier and is connected to the second measuring cell via a second diffusion barrier. The diffusion through these diffusion barriers is temperature-dependent, which leads to a temperature-dependent residual oxygen content in the second measuring cell. According to the prior art, it is attempted to remedy this by choosing the desired concentrations in the two measuring cells such that the second oxygen-ion pumping current for setting the oxygen concentration in the second measuring cell can be controlled to a fixed value, at which there is greatest possible temperature independence.

SUMMARY OF THE INVENTION

The object of the invention is to provide a method of determining a NO$_x$ concentration in a gas which overcomes the above-noted deficiencies and disadvantages of the prior art devices and methods of this kind, and which allows more exact sensing of the NO$_x$ concentration in a gas using the measuring sensor described above.

With the above and other objects in view there is provided, in accordance with the invention, a method of determining a NO$_x$ concentration in a gas, which comprises:

providing a measuring sensor with a a first measuring cell and a second measuring cell connected to the first measuring cell;

introducing a portion of a gas into the first measuring cell and adjusting a first oxygen concentration with a first oxygen-ion pumping current;

adjusting a second oxygen concentration in the second measuring cell with a second oxygen-ion pumping current;

measuring a NO$_x$ concentration with a measuring electrode in the second measuring cell;

correcting the measured value of the NO$_x$ concentration by a multiplicative correction value and an additive correction value, the correction values being taken from a characteristic map in dependence on at least the second oxygen-ion pumping current.

The novel method is particularly well suited for application in automotive exhaust systems. In that case, the sensor is exposed to the exhaust gas of an internal combustion engine and the NO$_x$ concentration in the exhaust gas of the internal combustion engine is measured.

In accordance with an added feature of the invention, the characteristic map is defined in a test bed measurement of the measuring sensor and thereby varying at least one parameter selected from the group consisting of a NO$_x$ concentration, a rate of change of the NO$_x$ concentration, an O$_2$ concentration, and a rate of change of the O$_2$ concentration.

In accordance with an additional feature of the invention, the characteristic map is defined in a test bed measurement of the measuring sensor under predetermined test gas conditions with the second oxygen-ion pumping current Ip1 being adjusted over a certain range.

In accordance with another feature of the invention, the characteristic map is additionally also dependent on a temperature of the measuring sensor and in addition, or alternatively, it is also dependent on a temperature of the gas to be measured.

In accordance with a concomitant feature of the invention, the temperature of the measuring sensor is the temperature at the second measuring cell.

In other words, according to the invention, the raw measured value supplied by the NO$_x$ measuring sensor is corrected by a multiplicative correction value f and an additive correction value a. Both correction values are taken from a characteristic map, which was preferably determined from the test bed measurement of the measuring sensor a measuring error depends on the second oxygen-ion pumping current Ip1. The improved measured value is then obtained by the following equation:

$$NO_x(\text{improved measured value}) = f \cdot NO_x(\text{raw measured value}) + a \quad (I).$$

The dependence of the correction factors on the oxygen-ion pumping current in the second measuring cell, which is a measure of the residual oxygen content in the second measuring cell, causing the measuring error, and preferably in addition on the temperature of the sensor, which is a measure of the diffusion through the diffusion barriers, and the gas temperature, as well as the evaluation of this dependence for the correction of the measured $NO_x$ raw measured value make it unnecessary furthermore for the second oxygen-ion pumping current to be controlled to a constant value.

Other features which are considered as characteristic for the invention are set forth in the appended claims.

Although the invention is illustrated and described herein as embodied in a method for determining $NO_x$ concentration, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
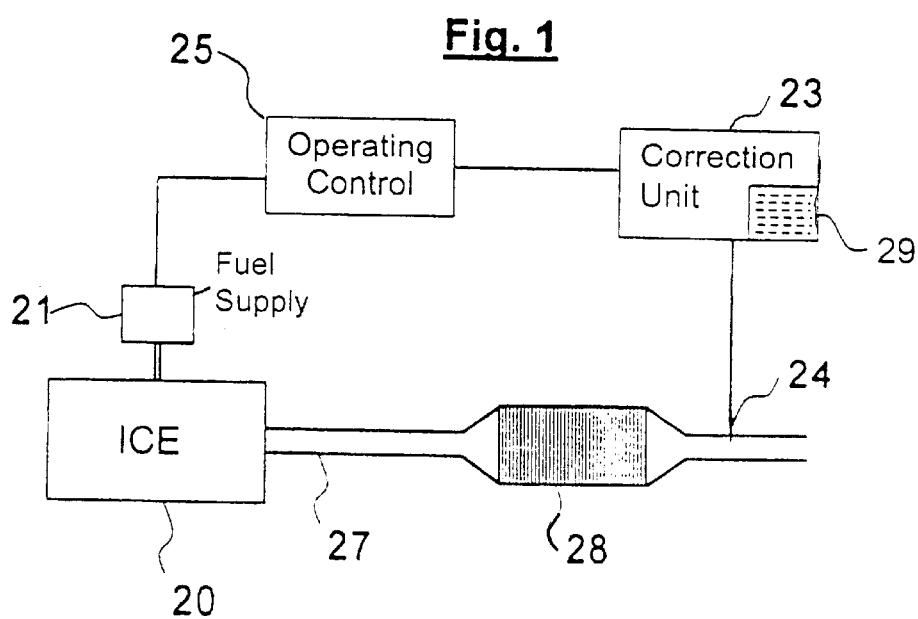
FIG. 1 is a schematic block diagram of a device for carrying out the method according to the invention.
Figure 2:
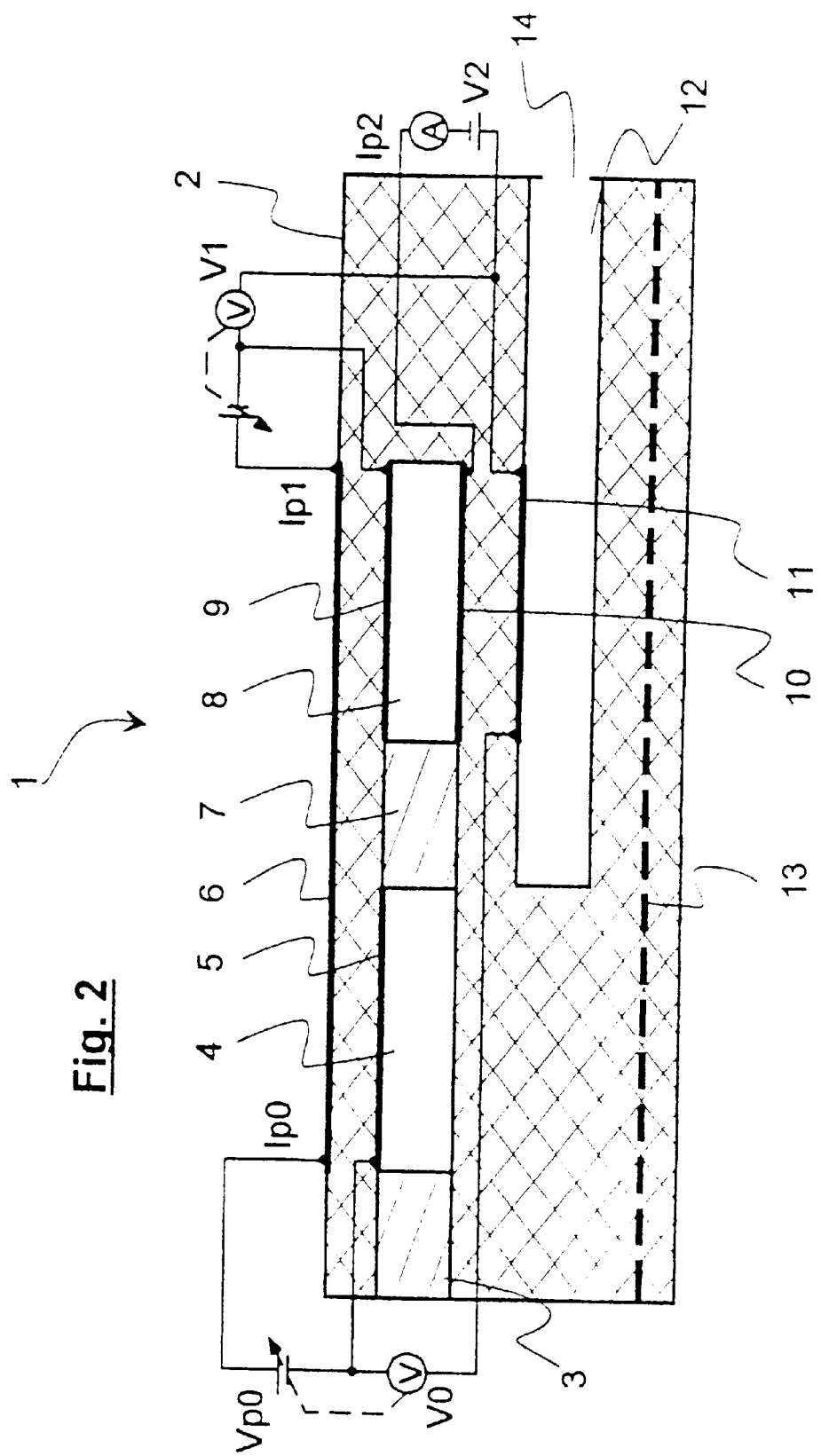
FIG. 2 is a schematic sectional view of an $NO_x$ measuring sensor.

Referring now to the figures of the drawing in detail, there is seen, in FIG. 2, a schematic section through an $NO_x$ measuring sensor 1. The measuring sensor 1 is used in the device represented in FIG. 1 as a measuring sensor 24 for determining the $NO_x$ concentration in the exhaust system 27 of an internal combustion engine 20. The raw measured value of the $NO_x$ measuring sensor 24 is corrected by a correction unit 23 by the method according to the invention and the corrected value is fed to the operating control device 25 of the internal combustion engine 20. The operating control device 25 uses the corrected $NO_x$ concentration measured value for activating the fuel supply system 21 of the internal combustion engine 20, so that an $NO_x$-reducing or $NO_x$-storing catalyst 28 has optimum operating characteristics.

The measuring sensor 1, which is disposed at position 24 in FIG. 1, is represented in a more detailed form in FIG. 2. The sensor 1 comprises a solid electrolyte 2, which is surrounded by the exhaust gas to be measured. The exhaust gas diffuses through a diffusion barrier 3 into a first measuring cell 4. The oxygen content in the measuring cell is measured by means of a first Nernst voltage V0 between a first electrode 5 and a reference electrode 11. The latter is exposed to ambient air. The reference electrode 11 is arranged in an air duct 12, for that purpose, into which ambient air enters via an opening 14.

Both electrodes are conventional platinum electrodes. The measured value of the first Nernst voltage V0 is used for setting a control voltage Vp0. The control voltage Vp0 drives a first oxygen-ion pumping current Ip0 through the solid electrolyte 2 between the first electrode 5 and an external electrode 6. The control intervention, represented by a dashed line, of the first Nernst voltage V0 on the control voltage Vp0 has the consequence that the first oxygen-ion pumping current Ip0 is controlled in such a way that there is a predetermined first oxygen concentration in the first measuring cell 4.

The first measuring cell 4 is connected to a second measuring cell 8 via a second diffusion barrier 7. The gas present in the measuring cell 4 diffuses through this diffusion barrier 7. The second oxygen concentration in the second measuring cell 8 is in turn measured via a second Nernst voltage V1 between a second electrode 9, which is likewise a platinum electrode, and the reference electrode 11 and is used for controlling a second oxygen-ion pumping current Ip1. The second oxygen-ion pumping current Ip1 from the first measuring cell 8 runs from the second electrode 9 through the solid electrolyte 2 to the external electrode 6. With the aid of the second Nernst voltage V1, the second oxygen-ion pumping current Ip1 is controlled in such a way that there is a predetermined low, second oxygen concentration in the second measuring cell 8. The $NO_x$ not affected by the previous processes in the measuring cells 4 and 8 is then decomposed at the measuring electrode 10, which is formed in such a way that it is catalytically active, by applying the voltage V2 between the measuring electrode 10 and the reference electrode 11. The released oxygen is pumped through the solid electrolyte 2 in a third oxygen-ion pumping current Ip2 toward the reference electrode 11. If there is a sufficiently small residual oxygen content at the measuring electrode 10, the third oxygen-ion pumping current Ip2 is carried only by oxygen ions which originate from the decomposition of $NO_x$. The current Ip2 is consequently a measure of the $NO_x$ concentration in the measuring cell 8 and consequently in the exhaust gas to be measured.

The residual oxygen content in the measuring cell 8 is ideally zero. In reality, however, it is dependent on various operating conditions of the measuring sensor 1:

The diffusion through the diffusion barriers 3 and 7 is temperature-dependent. As a result, the second oxygen-ion pumping current Ip1, usually controlled to a fixed value, results in a varying residual oxygen content in the measuring cell 8, depending on the temperature of the measuring sensor. Furthermore, with great sudden changes in $NO_x$ concentration, the control of the first oxygen-ion pumping current Ip0 is not capable of immediately setting the predetermined first oxygen concentration in the first measuring cell 4, which in turn results in a higher residual oxygen content in the second measuring cell 8, and consequently a greater measuring error, on account of the restricted control rate for the second oxygen-ion pumping current Ip1.

The invention remedies this by correcting the raw measured value supplied by the measuring sensor 1, 24 in a correction unit 23 to an improved measured value, dependent on a characteristic map 29. This correction is carried out using a multiplicative correction value f and an additive correction value a according to the above-noted equation (I) (Improved $NO_x$ value equals raw measurement value times the correction factor f plus a). The correction values f, and a are provided in the correction unit 23 in the characteristic map 29 which is dependent on the second oxygen-ion pumping current Ip1, on the temperature of the gas to be measured and on the temperature of the measuring sensor 1.

The characteristic map originates from a test bed measurement of a measuring sensor 1, 24 and the temperature of the measuring sensor 1 is the temperature at the location of the second measuring cell 8.

In the case of the internal combustion engine 20, the temperature of the gas to be measured may be measured by means of an exhaust-temperature measuring sensor or be computationally determined by means of a temperature model. If appropriate, estimated values may also be used for the actual temperatures. Should the temperatures of the gas to be measured and the measuring sensor not be available from measuring instruments, the characteristic map depends only on the second oxygen-ion pumping current Ip1. Since the temperature of the measuring sensor 1 can be controlled to a constant target temperature by means of a heater 13, the multiplicative correction value f and the additive correction value a may also be determined directly as a function of the second oxygen-ion pumping current Ip1 and the temperature of the gas to be measured, and only this relationship evaluated.

The invention further allows the second oxygen-ion pumping current Ip1 to be controlled more freely, since the fixed adjustment of a predetermined value for Ip1 required by the prior art on account of the correction of the measuring error caused by Ip1 and on account of the temperature dependence is no longer required.

We claim:

1. A method of determining a $NO_x$ concentration in a gas, which comprises:

providing a measuring sensor with a first measuring cell and a second measuring cell connected to the first measuring cell;

introducing a portion of a gas into the first measuring cell and adjusting a first oxygen concentration with a first oxygen-ion pumping current;

inroducing gas at the first oxygen concentration from the first measuring cell into the second measuring cell and adjusting a second oxygen concentration in the second measuring cell with a second oxygen-ion pumping current;

decomposing $NO_x$ present in the gas at the second oxygen concentration within the second measuring cell;

pumping oxygen present in the gas after decomposition of $NO_x$ form the second measuring cell with a third oxygen-ion pumping current;

measuring a $NO_x$ concentration with a measuring electrode in the second measuring cell by measuring the third oxygen-ion pumping current to obtain a measured value of the $NO_x$ concentration; and correcting the measured value of the $NO_x$ concentration by the following equation:

$$NO_x = f \cdot NO_x' + a$$

wherein $NO_x'$ is the measured value of the $NO_x$ concentration and f and a are correction values taken from a characteristic map in dependence on at least the second oxygen-ion pumping current.

2. The method according to claim 1, which comprises exposing the sensor to exhaust gas of an internal combustion engine and measuring the $NO_x$ concentration in the exhaust gas of the internal combustion engine.

3. The method according to claim 1, which comprises defining the characteristic map in a test bed measurement of the measuring sensor and thereby varying at least one parameter selected from the group consisting of a $NO_x$ concentration, a rate of change of the $NO_x$ concentration, an $O_2$ concentration, and a rate of change of the $O_2$ concentration.

4. The method according to claim 1, which comprises defining the characteristic map in a test bed measurement of the measuring sensor under predetermined test gas conditions with the second oxygen-ion pumping current being adjusted over a certain range.

5. The method according to claim 1, wherein the correction values in the characteristic map are also dependent on a temperature of the measuring sensor.

6. The method according to claim 5, which comprises equating the temperature of the measuring sensor with the temperature at the second measuring cell.

7. The method according to claim 1, wherein the correction values in the characteristic map are also dependent on a temperature of the gas to be measured.

* * * * *